United States Patent [19]

Vahlenkamp et al.

[11] Patent Number: 4,659,842

[45] Date of Patent: Apr. 21, 1987

[54] PHTHALIC ANHYDRIDE PROCESS AND PRODUCT

[75] Inventors: Hans H. Vahlenkamp, Matawan; Frank A. Calabrese, Parsippany, both of N.J.

[73] Assignee: BASF Corporation, Wyandotte, Mich.

[21] Appl. No.: 746,412

[22] Filed: Jun. 19, 1985

[51] Int. Cl.$^4$ ............................................ C07D 307/89
[52] U.S. Cl. ..................................... 549/247; 549/250
[58] Field of Search ................................ 549/247, 250

[56] References Cited

U.S. PATENT DOCUMENTS

| | | | |
|---|---|---|---|
| 1,789,967 | 1/1931 | Daniels et al. | 549/247 |
| 1,806,715 | 5/1931 | Schwindt | 549/247 |
| 1,817,304 | 8/1931 | Foster | 549/247 |
| 1,837,869 | 12/1931 | Jewett et al. | 549/247 |
| 1,891,754 | 12/1932 | Daniels et al. | 549/247 |
| 1,891,891 | 12/1932 | Luft et al. | 549/247 |
| 2,064,468 | 12/1936 | Foster | 549/250 |
| 2,436,766 | 2/1948 | Davis | 549/247 |
| 3,326,941 | 6/1967 | Campagne | 549/250 |
| 4,238,428 | 12/1980 | Sasaki et al. | 264/13 |
| 4,435,581 | 3/1984 | Miserlis | 549/250 |

OTHER PUBLICATIONS

George et al., Journal of Crystal Growth, vol. 37, No. 2 (1977), pp. 189-193.

*Primary Examiner*—Richard L. Raymond
*Attorney, Agent, or Firm*—William G. Conger; Joseph D. Michaels

[57] ABSTRACT

A phthalic anhydride product having a particle configuration made up of a mixture of spheroids, needle-like crystals, and amorphous particles is produced by feeding molten phthalic anhydride at a temperature between 131° and 155° into a spray nozzle in a closed cycle congealing chamber. The molten phthalic anhydride is discharged from the spray nozzle into a co-current or counter-current flow of inert gas at a temperature between −10° and 70° C., in order to congeal the product, which is then removed and transferred to a hopper or other storage means. For nozzle orifices having a diameter from 1 to 4 mm, discharge pressures of between 10 and 300 pounds per square inch are employed. In an especially preferred embodiment, the needle-like crystalline configurations are disjoined from the spheroids, thereby increasing the bulk density of the product, which in all embodiments exhibits the combination of superior flowability and more rapid dissolution, when compared with prior art products.

6 Claims, 4 Drawing Figures

PHTHALIC ANHYDRIDE PROCESS AND PRODUCT

BACKGROUND OF THE INVENTION

1. Field of the Invention

The present invention relates generally to processes for plastic and non-metallic article shaping, and to the shaped articles themselves. It relates in particular to (1) processes wherein material in the liquid state is comminuted and then solidified in comminuted form, the comminution being effected by causing the liquid to flow through a forming orifice; and (2) the comminuted products resulting from such processes.

2. Prior Art

The closest art known to applicants is as follows:

1. U.S. Pat. No. 1,789,967 discloses a comminuted crystalline phthalic anhydride product in the form of a "flour", i.e., a soft powder prepared by the grinding of phthalic anhydride crystals.

2. U.S. Pat. No. 2,064,468 relates to a finely-divided phthalic anhydride product, esp. microscopic needle-like crystals, produced by cooling phthalic anhydride vapor and diluting the same with an inert gas.

3. U.S. Pat. No. 1,817,304 gives details concerning a flaked phthalic anhydride product, which is made by distilling crude phthalic anhydride and introducing the liquid distillate into a standard flaking apparatus.

4. U.S. Pat. No. 1,837,869 discloses phthalic anhydride shot-like pellets having a hard surface glaze, the pellets being prepared from molten phthalic anhydride which has been sprayed counter to a rising stream of cooled air in a shot tower.

5. U.S. Pat. No. 4,238,428 relates to a process for making a prilled product from substances which are difficult to handle in powder form. This process comprehends the spraying of the melted substance from the top of a tower and the solidifying of the dropping liquid particles by means of a countercurrent gas introduced at the bottom of the tower. A special filter system provides a continuous, uninterrupted operation.

Unlike the configuration of any of the phthalic anhydride products disclosed in these prior art patents—viz., "flour", needle-like crystals, flakes, pellets—the configuration of the product of the instant invention is spheroidal in combination with amorphous and needle-like cyrstalline components. In a preferred embodiment of the product of the present invention, the needle-like crystalline components are disjoined from the spheroids, thereby enhancing the bulk density of the product. In all embodiments, however, the product of the present invention exhibits the heretofore unobtainable combination of superior flowability and more rapid dissolution, when compared with products of the prior art.

Unlike the general process disclosed in U.S. Pat. No. 4,238,428, the specific process of the present invention as claimed is particularly pointed to the production of a phthalic anhydride product having a novel configuration which will provide the combination of superior flowability and more rapid dissolution, when compared to prior art products.

SUMMARY OF THE PRESENT INVENTION

It is accordingly the primary object of the present invention to provide what is not available in the prior art, viz., a phthalic anhydride product having a particle configuration which results in superior flowability of the product in combination with more rapid dissolution thereof in standard solvents, when compared with the phthalic anhydride products available commercially. This object is achieved by the provision of phthalic anhydride in the form of a mixture of spheroids, needle-like crystalline configurations, and amorphous particles, the mixture having a bulk density of 450–700 grams per liter and a particle size of 100–700 microns. In an especially preferred embodiment of the product of the instant invention, the needle-like crystalline configurations are disjoined from the spheroids, resulting in an enhanced bulk density of the product.

The highly desirable product is provided by a process which comprises:

A. Feeding molten phthalic anhydride at a temperature between about 131° and 155° C. into a spray nozzle in a closed cycle congealing chamber, and discharging the molten phthalic anhydride from the spray nozzle, at a pressure of 10–300 pounds per square inch for nozzle orifices having a diameter from 1.0 to 4.0 mm, into a co-current or counter-current flow of inert gas at a temperature of about −10° to 70° C. to remove heat and congeal the product;

B. Exhausting gas from the congealing chamber and passing the exhausted gas into a cyclone separator; and C. Passing the exhaust gas from the cyclone separator through a standard cooling system to remove heat therefrom so that the temperature thereof is lowered to about −10° to 70° C., whence it is introduced into the congealing chamber in a co-current or counter-current flow; and D. Removing the congealed phthalic anhydride product and transferring the product to a hopper or other storage means.

In a preferred embodiment of this process, disjoining of the needle-like crystalline configurations from the spheroids of the phthalic anhydride product is accomplished by transferring the product removed from the congealing chamber into a screw conveyor and conveying the product therein to a hopper or other storage means.

In another preferred embodiment of this process, disjoining of the needle-like crystalline configurations from the spheroids of the phthalic anhydride product is accomplished by transferring the product removed from the congealing chamber into a cyclone separator, wherein the product is subjected to turbulent flow of inert gas.

Yet another preferred embodiment additionally comprises rotary air lock means in cooperation with the congealing chamber and cyclone separator for minimizing inert gas losses upon removal of phthalic anhydride product from the congealing system.

BRIEF DESCRIPTION OF THE DRAWINGS

For a more complete understanding of the present invention, including its primary object and benefits, reference should be made to the Detailed Description of the Preferred Embodiments, which is set forth below. This detailed description should be read together with the accompanying Drawings, wherein.

DETAILED DESCRIPTION OF THE PREFERRED EMBODIMENTS

Figure 1:
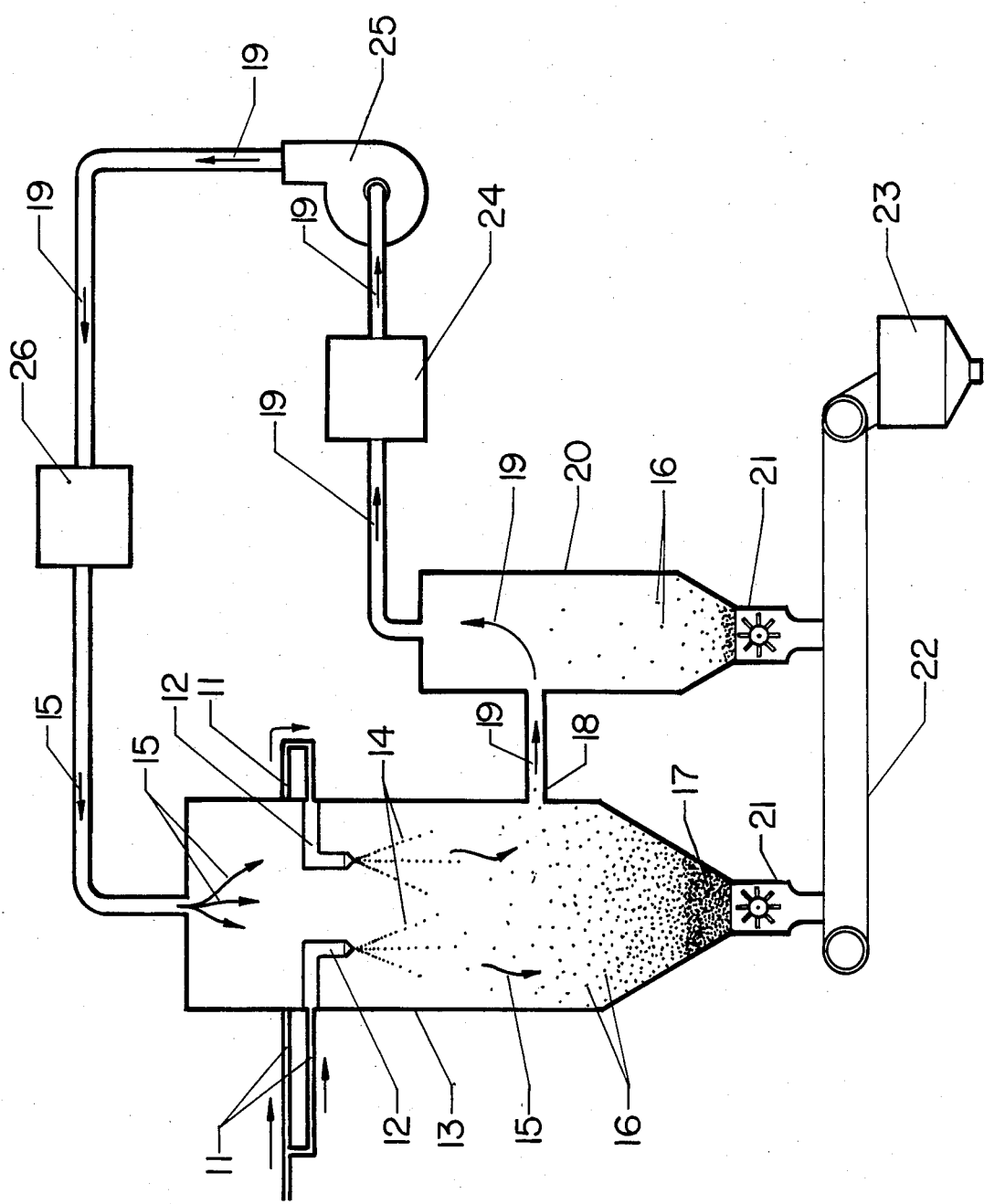
FIG. 1 is a schematic which details a preferred embodiment of the process according to the present invention.

Referring now to the Drawings, FIG. 1 shows molten phthalic anhydride 11 being fed into spray nozzles 12 in closed cycle congealing chamber 13. The phthalic anhydride, which has been prepared by any standard process (see Faith, Keyes & Clark's *Industrial Chemicals*, Wiley-Interscience, New York, 4th ed., 1975, ppg. 658–665), is heated to a temperature of between about 131° and 155° C. before introduction into the spray nozzle. The closed cycle congealing chamber is a standard pressurized vessel, e.g., of stainless steel. The spray nozzle is advantageously of the configuration detailed in U.S. Pat. No. 2,645,525, which is available at Niro Atomizer, Inc., Columbia, Md. 21045, U.S.A. The molten phthalic anhydride is discharged as a molten spray from the spray nozzle as at 14, at a pressure within the range of 10–300 pounds per square inch—for nozzle orifices having diameters from 1.0 to 4.0 mm—into a counter-current, or co-current flow (as shown) of inert gas 15, such as nitrogen, which is at a temperature within the range of −10° to 70° C. Heat is thereby removed from the molten phthalic anhydride, and the congealed product 16 collects as at 17 at the bottom of congealing chamber 13.

The inert gas is exhausted at 18 from congealing chamber 13, and the exhaust gas 19 is drawn into standard cyclone separator 20 by means of blower 25. Inside cyclone separator 20, entrained particles of the congealed phthalic anhydride product 16 are separated from exhaust gas 19, and are collected at the bottom of cyclone separator 20. Such product particles, along with those collected at the bottom of congealing chamber 13, are removed and forwarded to hopper 23 or other storage means for subsequent sale or use. Rotary air locks 21, which are well known and readily available, are advantageously employed to minimize loss of inert gas upon removing the congealed phthalic anhydride product from the congealing chamber and cyclone separator.

In a specially preferred embodiment, the needle-like crystalline configurations of the congealed phthalic anhydride product are disjoined from the spheroid components thereof by transferring the products removed from congealing chamber 13 and cyclone separator 20 into standard screw conveyor 22 prior to passage into hopper 23. Such a disjoining of these product components results in enhanced bulk density of the final product.

Exhaust gas 19 leaves cyclone separator 20 at the top thereof, and is drawn through filter 24 before entering blower 25, whence it is circulated through standard gas cooling system 26. Therein heat is removed from the inert gas so that the temperature thereof is lowered within the range −10° to 70° C., whence the inert gas as at 15 is introduced into congealing chamber 13 in a counter-current, or co-current flow as shown.

Figure 2:
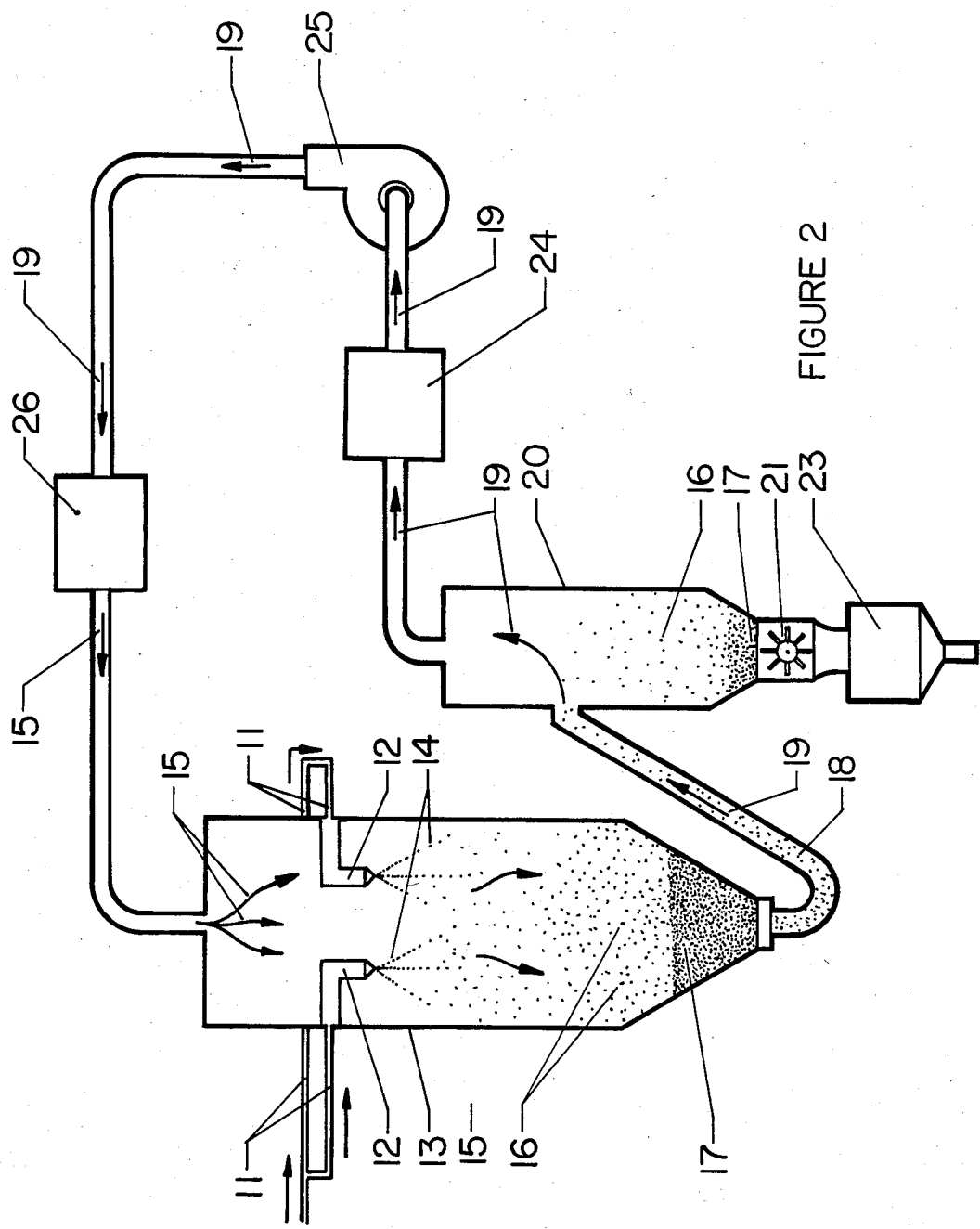
FIG. 2 is a schematic which details another preferred embodiment of the process according to the present invention.

Referring now to FIG. 2, there is shown another particularly preferred embodiment of the process of the present invention. This embodiment is identical to that pictured and described above with reference to FIG. 1, except that the exhaust of inert gas at 18 is effected at the bottom of congealing chamber 13, so that the exhausted gas 19 carries with it into cyclone separator 20 all of the congealed product 16 which is being collected in congealing chamber 13 at 17. Efficient separation of inert gas from particulates is effected in cyclone separator 20. Moreover, the turbulent flow of inert gas inside cyclone separator 20 serves to disjoin the needle-like crystalline configurations of the instant product from the spheroids thereof, thereby enhancing the bulk density thereof. The product is collected in cyclone separator 20 at 17 and passed through rotary air lock 21 into storage hopper 23. The inert gas 19, which has been freed of almost all particulates, is passed through filter 24 to remove any remaining particulates, and then into blower 25 (as described with reference to FIG. 1), whence it is circulated through cooling system 26 for entry into congealing chamber 13 as co-current flow 15.

Figure 3:
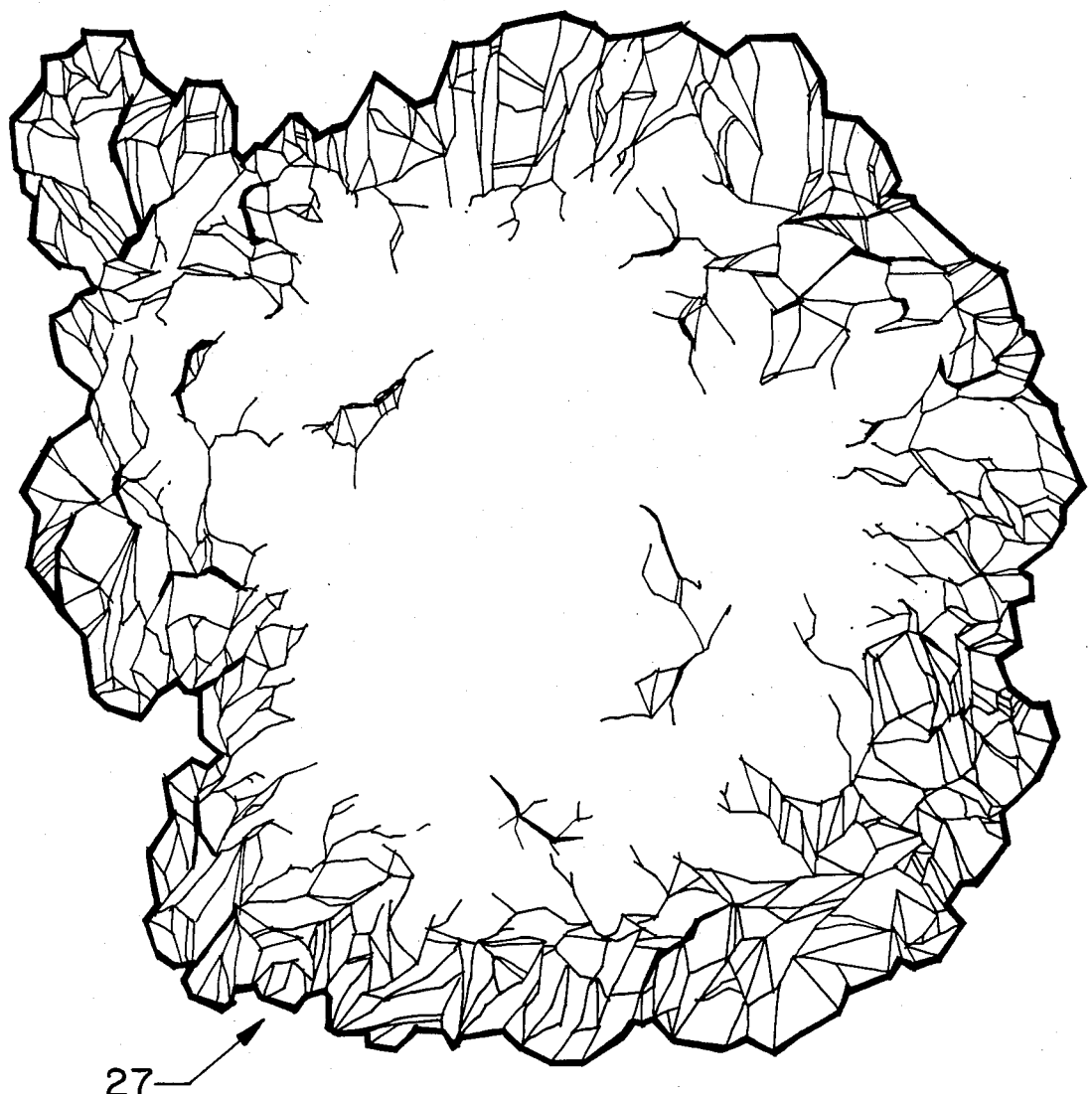
FIG. 3 is a schematic which pictures a particle of a phthalic anhydride product of the prior art as seen under the microscope.

The embodiments of the process of the present invention as detailed above result in a phthalic anhydride product which is decidedly and unexpectedly different from any available in the prior art. As an example of such prior art products, there is schematically depicted in FIG. 3 a particle 27 of flaked phthalic anhydride, as viewed under the microscope. This particle is in actuality an agglomerate or loosely held cluster of smaller crystalline units, as is seen from the depiction. In sharp contrast thereto is the product of the present invention, a microscopic depiction of which is shown as 17 in FIG. 4, at the same power of magnification as that employed in FIG. 3. The instant phthalic anhydride product 17 is a mixture of spheroids 28, amorphous particles 29, and needle-like crystalline configurations 30. In one embodiment of the instant product, a preponderance of the needle-like crystalline configurations are joined or fused to the spheroids. In another embodiment, the needle-like crystalline configurations are disjoined from the spheroids, the latter embodiment having a higher bulk density than the former. All embodiments of the present product have a bulk density within the range of 450–700 grams per liter, and a particle size within the range of 100–700 microns. The product is eminently suitable for use in the production of: dialkyl phthalates and other plasticizers; alkyd resins; hardeners for resins; polyesters; phenoephthalein and other phthaleins; pharmaceutical intermediates; and insecticides.

As desired by users of the instant product, the flowability thereof is excellent when compared with that of prior art products presently available. Moreover, the rate of dissolution of the instant product—which is one of the most important parameters considered by the user—is much faster than that of prior art products presently available.

To further illustrate the present invention in its especially preferred embodiments, the following Example is provided showing the best mode known to the inventors.

EXAMPLE

Figure 4:
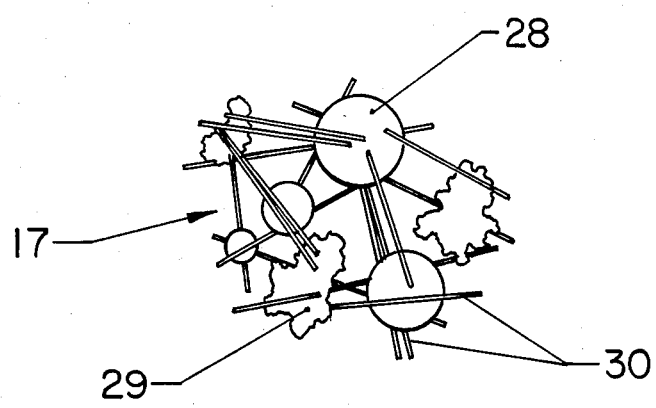
FIG. 4 is a schematic which portrays the particles of the phthalic anhydride product of the present invention as observed under the microscope.

A congealing system according to FIG. 1 was employed. Molten phthalic anhydride at 133° C. was fed at a rate of about 400 lbs/hr into a single spray nozzle as detailed in U.S. Pat. No. 2,645,525. A cooled inert gas stream (e.g., nitrogen) was employed in a co-current flow at a rate of about 1000 kg/hr. The inlet gas temperature was 14° C. and the outlet gas temperature was 46° C. The molten phthalic anhydride was discharged from the spray nozzle at a pressure of about 80 pounds per square inch, the nozzles having orifices of about 2 mm in diameter. An oxygen analyzer in cooperation with an inert gas control valve maintained the oxygen content of the system below 10 percent. After being exhausted from the top of the cyclone separator, the inert gas stream was passed through a filter to remove fines and then through an indirect contact cooling system to lower its temperature from about 46° C. at entrance to about 14°-15° C. at exit. About 99 percent of the product was removed from the bottom of the congealing chamber by means of a rotary air lock and passed into a standard screw conveyor on its way to a storage hopper. The remaining 1 percent of the product was removed from the bottom of the cyclone separator by means of a rotary air lock and passed to the screw conveyor on its way to the storage hopper. The final product had a particle size of between 100 and 500 microns and a bulk density of about 600 grams per liter. It consisted of a mixture of spheroids, amorphous particles, and needle-like crystals as shown in FIG. 4. Its average rate of dissolution in 2-ethylhexanol was 2 minutes and 30 seconds—as compared with an average rate of 5 minutes and 10 seconds for a flaked phthalic anhydride product having particles like that depicted in FIG. 3—according to the following test procedure:

PHTHALIC ANHYDRIDE RATE OF DISSOLUTION TEST

Apparatus
1. Programmable hot plate.
2. 600 ml Standard pyrex beaker.
3 Magnetic stirring bar (1½"×⅜").

Procedure
1. Program hot plate for a constant temperature of 80° C. and an agitator speed of 400 rpm.
2. Weigh into beaker 300 grams of 2-ethylhexanol and heat on hot plate to 80° C.
3. Once a constant temperature is reached, transfer 10 grams of phthalic anhydride product into the beaker and start stopwatch.
4. Observe solids in beaker.
5. Report time elapsed once a clear solution is obtained (i.e., one free of solid particles).

The present invention has been described in detail with respect to certain preferred embodiments thereof. As is understood by those of skill in the art, variations and modifications in this detail may be effected without any departure from the spirit and scope of the present invention, as defined in the hereto-appended claims.

We claim:

1. A process for producing a phthalic anhydride product having a novel particle configuration comprising spheroids, needle-like crystalline configurations, and amorphous particles; the process comprising:
    A. feeding molten phthalic anhydride at a temperature between about 131° and 155° C. into a spray nozzle in a closed cycle congealing chamber, and discharging the molten phthalic anhydride from the spray nozzle, at a pressure of 10-300 pounds per square inch for nozzle orifices having a diameter from 1.0 to 4.0 mm, into a flow of inert gas at a temperature of about −10° to 70° C. to remove heat and congeal the product;
    B. exhausting gas from the congealing chamber and passing the exhausted gas into a cyclone separator; and
    C. passing the exhaust gas from the cyclone separator through a standard cooling system to remove heat therefrom so that the temperature thereof is lowered to about −10° to 70° C., whence it is introduced into the congealing chamber; and
    D. removing the congealed phthalic anhydride product and transferring the product to a hopper or other storage means.

2. The process of claim 1, which additionally comprises disjoining the needle-like crystalline configurations from the spheroids of the phthalic anhydride product, thereby increasing the bulk density thereof.

3. The process of claim 2, wherein the disjoining of the needle-like crystalline configurations from the spheroids of the phthalic anhydride product is accomplished by transferring the product removed from the congealing chamber into a screw conveyor and conveying the product therein to a hopper or other storage means.

4. The process of claim 2, wherein the disjoining of the needle-like crystalline configurations from the spheroids of the phthalic anhydride product is accomplished by transferring the product removed from the congealing chamber into a cyclone separator, wherein the product is subjected to turbulent flow of inert gas.

5. The process of claim 1, which additionally comprises rotary air lock means in cooperation with the congealing chamber and cyclone separator for minimizing inert gas losses upon removal of phthalic anhydride product from the congealing system.

6. Phthalic anhydride in the form of a mixture of spheroids, needle-like crystalline configurations, and amorphous particles, the mixture having a bulk density of 450-700 grams per liter and a particle size of 100-700 microns.

* * * * *